US012203061B2

(12) United States Patent
Jose et al.

(10) Patent No.: US 12,203,061 B2
(45) Date of Patent: Jan. 21, 2025

(54) SYSTEM AND METHOD FOR ENABLING A SINGLE USE WIRELESS SENSOR BY OPTIMIZING ELECTRICAL POWER

(71) Applicant: Cytiva Sweden AB, Uppsala (SE)

(72) Inventors: Victor Jose, Bangalore (IN); Veena B N Rao, Bangalore (IN); Hanish Lakhani, Bangalore (IN)

(73) Assignee: Cytiva Sweden AB, Uppsala (SE)

( * ) Notice: Subject to any disclaimer, the term of this patent is extended or adjusted under 35 U.S.C. 154(b) by 1069 days.

(21) Appl. No.: 16/605,115

(22) PCT Filed: Apr. 18, 2018

(86) PCT No.: PCT/EP2018/059810
§ 371 (c)(1),
(2) Date: Oct. 14, 2019

(87) PCT Pub. No.: WO2018/197274
PCT Pub. Date: Nov. 1, 2018

(65) Prior Publication Data
US 2020/0399582 A1    Dec. 24, 2020

(30) Foreign Application Priority Data
Apr. 28, 2017 (IN) .............................. 201741015121

(51) Int. Cl.
*C12M 1/00* (2006.01)
*C12M 1/21* (2006.01)
(Continued)

(52) U.S. Cl.
CPC ............ *C12M 23/14* (2013.01); *C12M 23/28* (2013.01); *C12M 41/02* (2013.01); *C12M 41/12* (2013.01);
(Continued)

(58) Field of Classification Search
CPC ...... C12M 41/48; C12M 41/02; C12M 41/12; C12M 41/26; C12M 41/32; C12M 41/34;
(Continued)

(56) References Cited

U.S. PATENT DOCUMENTS

2004/0085562 A1    5/2004   Fromherz
2005/0254055 A1*  11/2005  Peng ...................... C12M 41/36
                                                                356/432
(Continued)

FOREIGN PATENT DOCUMENTS

CN    102656282 A    9/2012
CN    101331503 A    12/2012
(Continued)

OTHER PUBLICATIONS

PCT International Search Report and Written Opinion for PCT Application No. PCT/EP2018/059810 mailed Jul. 19, 2018 (10 pages).

(Continued)

*Primary Examiner* — Michael L Hobbs
(74) *Attorney, Agent, or Firm* — Eversheds-Sutherland (US) LLP (57) ABSTRACT

A system for enabling a wireless single use sensing sub-system by optimizing electrical power is presented. The system includes the sensing sub-system configured to be employed in a bio process environment. Further, the sensing sub-system includes a sensing unit configured to measure at least one parameter of the bio process environment. Also, the sensing sub-system includes a power source electrically coupled to the sensing unit and configured to transmit an electrical power to the sensing unit. Furthermore, the sensing sub-system includes a switch configured to electrically couple or decouple the sensing unit from the power source. In addition, the system includes a control sub-system includ- (Continued)

ing a first controller configured to determine at least one power control parameter based on a user-input data and a sensing sub-system data, and optimize consumption of the electrical power in the sensing sub-system, based on the power control parameter.

24 Claims, 6 Drawing Sheets

(51) Int. Cl.
  *C12M 1/34*   (2006.01)
  *C12M 1/36*   (2006.01)
  *C12Q 1/02*   (2006.01)
  *H02J 7/00*   (2006.01)

(52) U.S. Cl.
  CPC ............ *C12M 41/26* (2013.01); *C12M 41/32* (2013.01); *C12M 41/34* (2013.01); *C12M 41/40* (2013.01); *C12M 41/46* (2013.01); *C12M 41/48* (2013.01); *C12Q 1/02* (2013.01); *H02J 7/0063* (2013.01)

(58) Field of Classification Search
  CPC ...... C12M 41/40; C12M 41/46; C12M 41/00; C12M 23/14; C12M 23/28; C12Q 1/02; H02J 7/0063
  See application file for complete search history.

(56) References Cited

U.S. PATENT DOCUMENTS

| | | |
|---|---|---|
| 2007/0243626 A1 | 10/2007 | Windeyer et al. |
| 2008/0069739 A1 | 3/2008 | Ludwig |
| 2009/0176301 A1* | 7/2009 | Oldenburg ............ C12M 27/02 435/297.1 |
| 2010/0144022 A1 | 6/2010 | Surapaneni |
| 2012/0187897 A1 | 7/2012 | Lenk et al. |
| 2013/0193774 A1 | 8/2013 | Yang et al. |
| 2014/0175876 A1* | 6/2014 | Cheatham, III ........ H02J 50/80 307/23 |
| 2014/0212954 A1 | 7/2014 | Auner et al. |
| 2014/0255910 A1* | 9/2014 | Arnold ...................... H02J 3/14 435/286.1 |
| 2014/0287449 A1* | 9/2014 | Bonyuet .................. C12Q 1/02 435/29 |
| 2015/0128733 A1 | 5/2015 | Taylor et al. |
| 2015/0137992 A1* | 5/2015 | Potyrailo ......... G06K 19/07745 340/870.07 |
| 2017/0039441 A1 | 2/2017 | Lim et al. |

FOREIGN PATENT DOCUMENTS

| | | |
|---|---|---|
| CN | 102859527 A | 1/2013 |
| CN | 105471123 A | 4/2016 |
| CN | 104769766 A | 4/2018 |
| EP | 2774979 A1 | 9/2014 |
| EP | 2822144 A1 | 1/2015 |
| JP | 2015123300 A | 7/2015 |
| WO | 2013096842 A2 | 6/2013 |
| WO | 2016/037100 A1 | 3/2016 |

OTHER PUBLICATIONS

European Office Action for EP Application No. 18718446.0 mailed Nov. 30, 2020 (7 pages).
European Office Action for EP Application No. 18718447.8 mailed Dec. 2, 2020 (7 pages).
"BioProcess Product Guide 2012/2013", GE Healthcare Life Sciences, 2014, pp. 1-20.
"Integrated Bioprocess Solutions", Millipore Sigma, 2016, pp. 1-24.
International Search Report for PCT Application No. 2018/059811 mailed Jul. 26, 2018 (8 pages).
International Search Report for PCT Application No. 2018/059809 mailed Aug. 21, 2018 (10 pages).
Wikipedia contributors. (Aug. 25, 2022). Wireless. In Wikipedia, The Free Encyclopedia. Retrieved 17:11, Aug. 30, 2022, from https://en.wikipedia.org/w/index.php?title=Wireless&oldid=1106637765.
China National Intellectual Property Administration (CNIPA), First Office Action & Search Report for CN Application No. 20188027625.3 dated Feb. 2, 2023, (35 pages, including Reporting Letter and English translations).
China National Intellectual Property Administration (CNIPA), First Office Action & Search Report for CN Application No. 201880027789.6 dated Jan. 20, 2023, (36 pages including English translations).

* cited by examiner

SYSTEM AND METHOD FOR ENABLING A SINGLE USE WIRELESS SENSOR BY OPTIMIZING ELECTRICAL POWER

CROSS REFERENCE TO RELATED APPLICATIONS

This application claims the priority benefit of PCT/EP2018/059810 filed on Apr. 18, 2018, which claims priority benefit of Indian patent application No. 201741015121 filed on Apr. 28, 2017, the entire contents of which are hereby incorporated by reference herein.

BACKGROUND

Embodiments of the present specification relate generally to a bioprocess environment, and more particularly to systems and methods for enabling a single use wireless sensor by optimizing electrical power.

Typically, in a bioprocess environment, a series of actions or steps are taken in a prescribed sequence on living cells, or their molecular components, such as proteins, deoxyribonucleic acid (DNA), and peptides to develop and/or purify one or more desired products. These series of actions or steps is known as bioprocess operation in the bioprocess environment. However, a proper control and monitoring of the bioprocess operation is required to develop these desired products.

Many bioprocess systems use equipment to monitor and control the bioprocess operation. In one example, the equipment includes filters, circuits, disposable components, and the like. Also, these components have tubing connection between them to convey fluid from one component to another. Further, wired sensors are disposed on the components and/or the tubing connection to measure parameters in the bioprocess environment. Some of these parameters include temperature, pressure, a potential of hydrogen (pH), and dissolved oxygen (DO) in the fluid. Further, these wired sensors are connected to an external reader using elongated and/or interconnecting wires to track the measured parameters.

Furthermore, due to wired connections, there are limitations or challenges to position the sensors at desired locations in the bioprocess environment. Moreover, the wired connections may restrict the usage of the reader to interface with a limited number of sensors, which in-turn may make the existing systems non-scalable. In addition, the reader may be bulky in size and occupy additional space in the bioprocess system. Also, these interconnecting wires between the sensors and the reader may cause inconvenience to a user to perform the bioprocess operation. Moreover, a recurring cost of wiring between the sensors and the reader may occur when scaling the bioprocess system.

Thus, there is a need for an improved system and method to monitor and control the bioprocess in the bioprocess environment.

BRIEF DESCRIPTION

In accordance with aspects of the present specification, a system is presented. The system includes a sensing sub-system configured to be employed in a bioprocess environment. Further, the sensing sub-system includes at least one sensing unit configured to measure at least one parameter of the bioprocess environment. Alternatively, or additionally, the sensing sub-system may include a pair of sensing units where each unit is embedded in one part of a connector for connection of tubing, or bioprocess devices. In this case, the sensing units are configured to recognize when the connector parts are correctly mated to provide a secure connection between the right components. Also, the sensing sub-system includes a power source electrically coupled to the sensing unit and configured to transmit an electrical power to the sensing unit. Furthermore, the sensing sub-system includes a switch configured to electrically couple or decouple the sensing unit from the power source. In addition, the system includes a control sub-system including a first controller configured to determine at least one power control parameter based on a user-input data and a sensing sub-system data, and optimize consumption of the electrical power in the sensing sub-system, based on the power control parameter.

In accordance with another embodiment of the present specification, a method for optimizing consumption of an electrical power in a sensing sub-system configured to be employed in a bioprocess environment is presented. The method includes measuring, by a sensing unit in the sensing sub-system, at least one parameter of the bioprocess environment. Also, the method includes determining, by a first controller in a control sub-system, at least one power control parameter based on a user-input data and a sensing sub-system data. Further, the method includes optimizing, by the first controller, consumption of the electrical power in the sensing sub-system based on the at least one power control parameter.

In accordance with another embodiment of the present specification, a system is presented. The system includes a plurality of wireless sensing sub-systems that are single-use and configured to be employed in a bioprocess environment, wherein each of the plurality of wireless sensing sub-systems includes a sensing unit configured to measure at least one parameter of the bioprocess environment. Also, each of the plurality of wireless sensing sub-system includes a power source electrically coupled to the sensing unit and configured to transmit an electrical power to the sensing unit. Further, each of the plurality of wireless sensing sub-systems includes a switch configured to electrically couple or decouple the sensing unit from the power source. In addition, the system includes a control sub-system wirelessly coupled to the plurality of wireless sensing sub-systems. Further, the control sub-system includes a first controller configured to determine at least one power control parameter based on a user-input data and a sensing sub-system data of a corresponding wireless sensing sub-system, and optimize consumption of the electrical power in the corresponding wireless sensing sub-system, based on the power control parameter.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various embodiments of systems and methods for enabling wireless sensing subs-systems by optimizing electrical power are presented. In some embodiments, the systems and methods presented herein employ the wireless sensing sub-systems and wireless control sub-systems to monitor and control a bioprocess operation in the bioprocess environment. Further, the consumption of the electrical power by these wireless sensing sub-systems is optimized based on data corresponding to a bioprocess application. By optimizing the consumption of the electrical power, the size of the power source, such as a battery in the wireless sensing sub-systems may be substantially reduced. This in-turn may reduce the size and the manufacturing cost of the wireless sensing sub-systems. In addition, the wireless sensing sub-systems may be positioned at more locations to measure more parameters, which in-turn enables better process control and analytics of the bioprocess operation.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. The use of terms "including," "comprising" or "having" and variations thereof herein are meant to encompass the items listed thereafter and equivalents thereof as well as additional items. The terms "connected" and "coupled" are not restricted to physical or mechanical connections or couplings and can include electrical connections or couplings, whether direct or indirect. Furthermore, terms "circuit," "circuitry," "controller," and "control unit" may include either a single component or a plurality of components, which are either active and/or passive and are connected or otherwise coupled together to provide the described function. In addition, the term operationally or operatively coupled as used herein includes wired coupling, wireless coupling, electrical coupling, magnetic coupling, radio communication, software based communication, or combinations thereof.

In some embodiments, a system including a sensing sub-system configured to be employed in a bioprocess environment is presented. The sensing sub-system includes a sensing unit configured to measure at least one parameter of the bioprocess environment. Alternatively, or additionally, the sensing sub-system may comprise a pair of sensing units, each embedded in a connector unit, and configured to detect when the connector units are correctly connected to each other. Also, the sensing sub-system includes a power source electrically coupled to the sensing unit and configured to transmit an electrical power to the sensing unit. Further, the sensing sub-system includes a switch configured to electrically couple or decouple the sensing unit from the power source. In addition, the system includes a control sub-system including a first controller configured to determine at least one power control parameter based on a user-input data and a sensing sub-system data, and optimize consumption of the electrical power in the sensing sub-system, based on the power control parameter.

Figure 1:
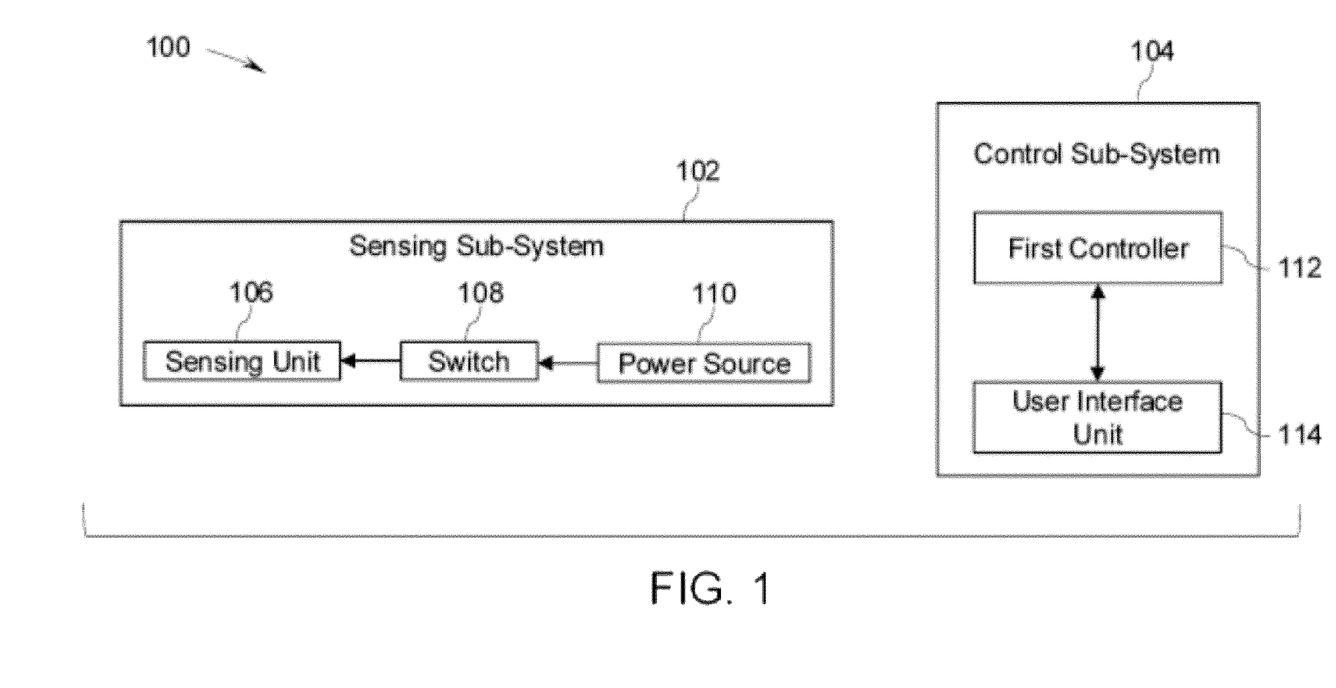
FIG. 1 is a block diagram of a system for enabling a wireless sensor by optimizing electrical power, in accordance with aspects of the present specification.

Turning now to the drawings and referring to FIG. 1, a block diagram of a system 100 for optimizing consumption of an electrical power in a bioprocess environment, in accordance with aspects of the present specification, is depicted. The bioprocess environment may be referred to as an environment that aids in performing a bioprocess operation to develop one or more desired products, such as vaccines, hormones, plasma proteins, monoclonal antibodies, pharmaceuticals, or combinations thereof.

In certain embodiments, the bioprocess environment may include biodevices, such as bioreactors, cell banking units, filters, cell harvesting units, chromatography units, circuits, wave rockers, protein concentration units, sterile filtration units, virus removal units, product holding units, buffer preparation units, media preparation units, buffer holding units, media holding units, pumps, flexible cell culture bags, mixers, tanks, safety units, other disposable components and the like. Also, some of these devices may be connected to each other with tubes, clamps, and smart switches that aid in conveying and controlling fluid from one device to another device.

Further, the bioprocess operation is performed using one or more of these devices in the bioprocess environment to develop and/or purify the desired products. It may be noted that bioprocess operation is referred to as a series of actions or steps that are taken in a prescribed sequence on living cells, organisms, or their molecular components in the fluid to develop the desired products in the bioprocess environment. Some of the bioprocess operations may include processing of genetically engineered organisms or cells to obtain the desired products.

As depicted in FIG. 1, the system 100 includes a sensing sub-system 102 and a control sub-system 104. The sensing sub-system 102 may also be referred to as a sensor and the terms "sensing sub-system" and "sensor" are used herein interchangeably. In certain embodiments, the sensing sub-system 102 is a wireless sensor that can measure one or more parameters and can communicate these measured parameters to an external device wirelessly.

In some embodiments, a portion of the sensing subsystem 102 may be single-use. For example, a sensing element in the sensing sub-system that is contact with a fluid is disposable after a cycle of bioprocess operation. It can suitably be pre-sterilized, e.g. by radiation sterilization. After disposing the sensing-subsystem, a new sensing element may be electrically coupled with existing components, such as a signal processor, a power source and a transceiver in the sensing sub-system for another cycle of bioprocess operation. The cycle of bioprocess operation is referred as a time taken to complete a series of actions or steps in a prescribed sequence to develop the desired product. The term "single-use" is referred as the usage of the device/component for only one cycle of bioprocess operation. After one cycle of bioprocess operation, the device/component is disposed.

In certain embodiments, the sensing sub-system 102 is a single-use device that is disposable after the cycle of bioprocess operation in the bioprocess environment. In such instances, all the components of the sensing sub-system 102 are single-use, that is, the entire sub-system is disposable. For example, if the sensing sub-system 102 is used in the bioreactors, the cycle of bioprocess operation in the bioreactors may last for several days. After completing the cycle of bioprocess operation, the sensing sub-system 102 is disposed and a new sensing sub-system is used for another cycle of bioprocess operation.

Since the sensing sub-system 102 is single use, it is desirable to reduce the cost and the size of the sensing sub-system 102, such that the overall cost to develop the desired products may be substantially reduced. Embodiments of the present specification may allow for power optimization in the sensors as described here. In certain embodiments, embodiments of the present specification may allow for power optimization in single-use, wireless sensors as described herein.

In one example, the sensing sub-system is a pressure sensor, a temperature sensor, a potential of hydrogen (pH) sensor, a conductivity sensor, a glucose sensor, a biomass sensor, a cell viability sensor, an oxygen sensor, a carbon-dioxide sensor, an ultraviolet (UV) sensor, a flow sensor, a foam sensor, or combinations thereof.

Further, the sensing sub-system 102 is configured to measure one or more parameters in the bioprocess operation. Some of the parameters include pressure of the fluid employed for one or more applications in the bioprocess environment, electrical conductivity of the fluid, a biomass in the fluid, a dissolved gas level in the fluid, temperature of the fluid, glucose flow in the fluid, a viable cell density in the fluid, a flow rate of the fluid, a level of foam in the fluid, and a potential of hydrogen (pH) level in the fluid. It may be noted that the sensing sub-system 102 may be positioned at any desired location, such as on the bioreactors, the filtration unit, the circuits, the disposable components, the flexible cell culture bags, the pumps, and the connecting tubes in the bioprocess environment.

Figure 2:
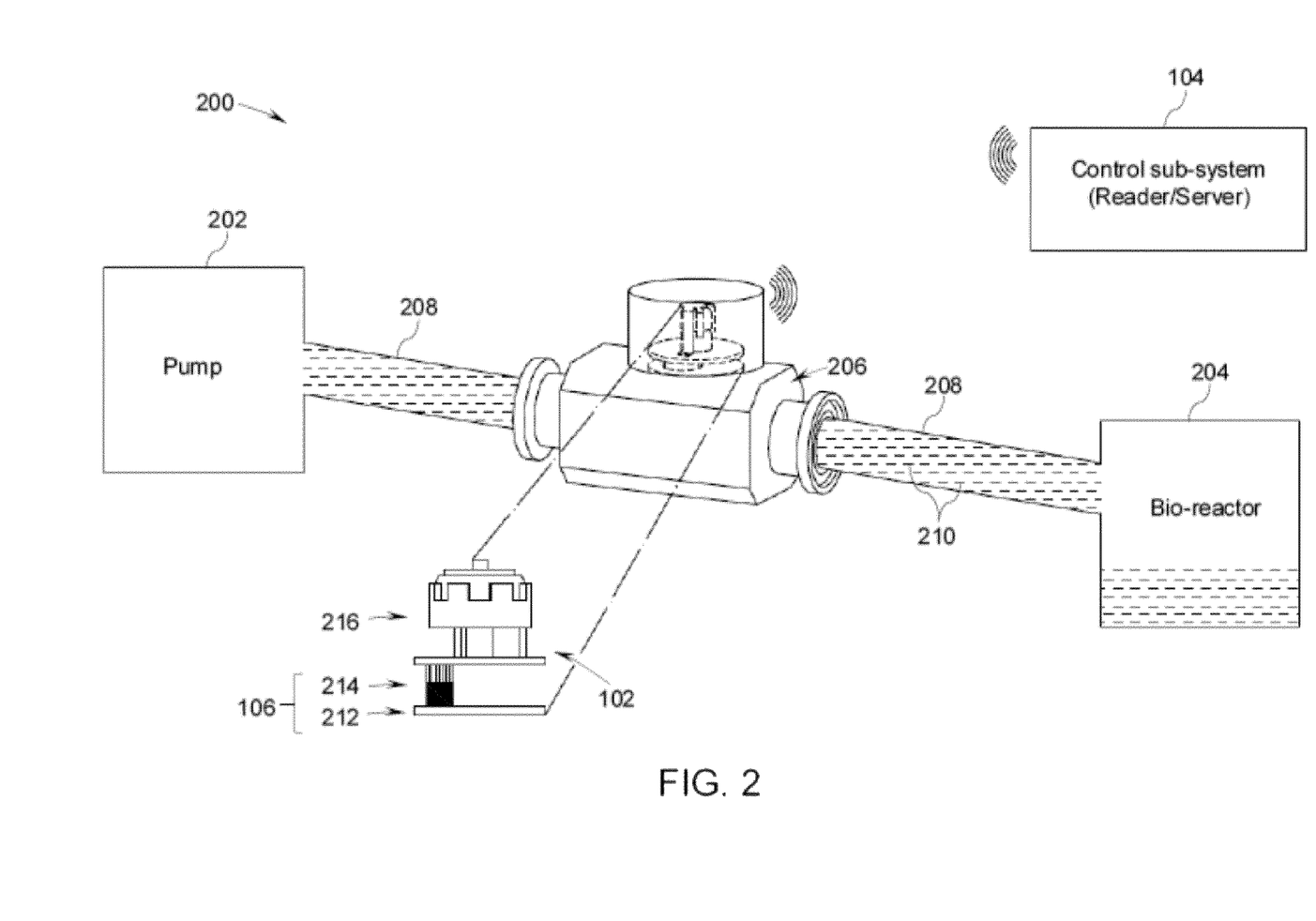
FIG. 2 is a diagrammatical representation of a bioprocess environment having a sensing sub-system and a control sub-system, in accordance with aspects of the present specification.

In some embodiments, the sensing sub-system 102 may be operatively coupled to the connecting tubes that are positioned between the pump and the bioreactors (shown in FIG. 2). Also, these sensing sub-systems 102 may be used as key building blocks of a flexible flow path. In the embodiment depicted in FIG. 2, the sensing sub-system 102 is configured to measure the parameters of the fluid that flows from the pump to the bioreactor via the connecting tube. However, the sensing sub-system 102 may be configured to be disposed in other components of the bioprocess environment as well, for example, in the bioreactor itself. In such embodiments, the sensing sub-system 102 may be configured to measure the parameters of the fluid that the sensing sub-system 102 is in contact with. It may be noted that a tubular structure of the connecting tubes and the coupling of the sensing sub-system 102 to this tubular structure are described in detail with reference to FIG. 2. Also, in certain embodiments, the sensing sub-system 102 is a single-use, wireless sensor.

In a presently contemplated configuration, the sensing sub-system 102 includes a sensing unit 106, a switch 108, and a power source 110. It may be noted that the sensing sub-system 102 may include other components, and is not limited to the components depicted in FIG. 1. In one example, the power source 110 may be a portable battery, such as a coin cell battery CR2032 with a nominal voltage of 3 V and energy capacity of 230 mAh. In certain embodiments, the power source 110 may be detachably coupled to other components in the sensing sub-system 102. Moreover, the power source 110 is used to provide electrical power to the components in the sensing sub-system 102. In accordance with embodiments of the disclosure, the components, such as the sensing unit 106 in the wireless sensing sub-system 102 may be enabled to optimize the consumption of electrical power from the power source 110 to complete the cycle of bioprocess operation. The wireless sensing sub-system 102 may be easily activated and deactivated based on the cycle of bioprocess operation, which in-turn aids in optimizing the consumption of electrical power from the power source 110.

Further, the sensing sub-systems in accordance with some embodiments of the specification may allow for modular sensors such that the sensor components can be designed and fitted together in variety of configurations. The modular sensor may be referred as a sensing device where one or more internal elements/components of the sensor may be separated or disintegrated from other internal elements/components in the sensor. In one embodiment, the sensing unit 106 may be disintegrated from the power source 110 and the switch 108. Also, a new sensing unit 106 may be integrated with the existing power source 110 and the switch 108 in the sensing sub-system 102.

Further, the switch 108 is configured to electrically couple or decouple the sensing unit 106 from the power source 110. If the switch 108 is activated, the sensing unit 106 is electrically coupled to the power source 110 to receive the electrical power from the power source 110. Also, the sensing unit 106 measures the parameters of the fluid after receiving the electrical power from the power source 110. In one example, the sensing unit 106 consumes the electrical power from the power source 110 while measuring or sensing the parameters of the fluid. More specifically, the electrical power from the power source 110 may be used as a bias voltage for activating the sensing unit 106 and measuring the parameters of the fluid. It may be noted that a mode of the sensing unit 106 where the sensing unit 106 is active is referred to as an active mode of the sensing unit 106.

In a similar manner, if the switch 108 is deactivated, the sensing unit 106 is electrically decoupled from the power source 110, which in turn ceases the consumption of the electrical power from the power source 110 by the sensing unit 106. Also, in some such instances, the sensing unit 106 may be switched to a sleep mode where the sensing unit 106 is inactive and is not measuring the parameters of the fluid.

Furthermore, the control sub-system 104 is operationally coupled to the sensing sub-system 102 to receive the measured parameters of the fluid from the sensing unit 106. In one example, the control sub-system 104 may receive one or more sensed signals that represent the measured parameters of the fluid. It may be noted that control sub-system 104 may be coupled to a plurality of sensing sub-systems, and is not limited to a single sensing sub-system 102 as depicted in FIG. 1.

In certain embodiments, the control sub-system 104 is wirelessly coupled to the sensing sub-system 102 to receive the measured parameters of the fluid from the sensing unit 106. The aspect of wirelessly coupling the control sub-system 104 to the sensing sub-system is described in detail with reference to FIG. 3. In one example, the control sub-system 104 may be wirelessly coupled to the sensing sub-system 102 using any wireless communication techniques, such as infrared, short-range radio frequency (RF) communication, Bluetooth, Bluetooth Low Energy (BLE), Wi-Fi, Wi-Max, Global System for Mobile (GSM), General Packet Radio Service (GPRS), Code Division Multiple Access (CDMA), High-Speed Downlink Packet Access (HSDPA), and the like.

Further, the control sub-system 104 includes a first controller 112 and a user interface unit 114 that are electrically coupled to each other. The user interface unit 114 may be referred to as an input-output (I/O) device that is configured to receive data from a user and/or display data to the user. In one embodiment, the user interface unit 114 is configured to receive a user-input data. The user-input data includes data indicating time duration of operating the sensing sub-system 102, application of the sensing sub-system 102, and/or at least one desired parameter of the fluid in the bioprocess environment. The application of the sensing sub-system 102 may include usage of the sensing sub-system 102 in the biodevices, such as the bioreactors, the filtration units, the chromatography units, the mixers/tanks, or the safety units. The time duration of operating the sensing sub-system 102 may include a cycle of bioprocess operation in the corresponding biodevices. In certain embodiments, the user may select one or more options from a drop-down menu in the user interface unit 114. These selected options may be used as the user-input data and/or the sensing sub-system data. Further, the user interface unit 114 transmits the user-input data to the first controller 112.

In a similar manner, the first controller 112 may receive a sensing sub-system data from the sensing sub-system 102. The sensing sub-system data includes data indicating a type of the sensing sub-system 102, an electrical power consumption of the sensing sub-system 102, and/or a power level in the power source 110 of the sensing sub-system 102. In one example, the data indicating the type of the sensing sub-system 102 may be used to identify the sensors, such as the pressure sensor, the temperature sensor, the pH sensor, the conductivity sensor, the glucose sensor, the biomass sensor, the cell viability sensor, the oxygen sensor, the carbon-dioxide sensor, the ultraviolet (UV) sensor, the flow sensor, and the foam sensor employed in the bioprocess environment. In one embodiment, the first controller 112 may receive the sensing sub-system data from a user via the user interface unit 114.

Upon receiving the user-input data and the sensing sub-system data, the first controller 112 determines one or more power control parameters based on the user-input data and the sensing sub-system data. Some of the power control parameters may include a transmission power value, a switching time value, a connection interval, a latency, a handshake power value, number of data bytes, and a parameter update rate associated with the sensing sub-system. The transmission power value indicates an optimal power level that is required by the sensing sub-system 102 to transmit the measured parameters of the fluid. Similarly, the switching time value indicates turn ON time and turn OFF time of the sensing unit 106 in the sensing sub-system 102. Also, the connection interval indicates a time duration during which the second transceiver 316 is activated or turned ON. The latency indicates the delay in transmitting data packets that represent the measured parameters. The handshake power value indicates an optimal power that is required by the sensing sub-system 102 to establish wireless communication between the sensing sub-system 102 and the control sub-system 104. Further, the number of data bytes indicates optimal data packets that are used for transmitting the measured parameters from the sensing sub-system 102. Also, the parameter update rate indicates a frequency of transmitting the measured parameters from the sensing sub-system 102.

In certain embodiments, the first controller 112 may employ a pre-stored set of instructions/algorithm along with the user-input data and the sensing sub-system data to determine the power control parameters. It may be noted that the method or algorithm employed to determine the power control parameters is described with reference to FIG. 6. Particularly, as depicted in step 602 of FIG. 6, the method begins with a step of receiving the user-input data and the sensing sub-system data by the first controller 112. Further, as shown in step 604, the first controller 112 determines the power control parameters using the user-input data and the sensing sub-system data. In one example, the first controller 112 may determine the connection interval based on a frequency data included in the user-input data. The frequency data indicates a rate at which the parameters of the fluid need to be communicated to the control sub-system. In one example, if the frequency data is 1 sec, the connection interval is half of the frequency data, which is 0.5 sec. Further, the first controller 112 may determine another power control parameter, such as the latency based on the connection interval and the frequency data. In one example, if the connection interval is 0.5 sec and the frequency data is 1 sec, the latency is the ratio of the frequency data to the connection interval, which is 2 sec. In a similar manner, the first controller 112 determines each of the power control parameters for the sensing sub-system 102.

Figure 6:
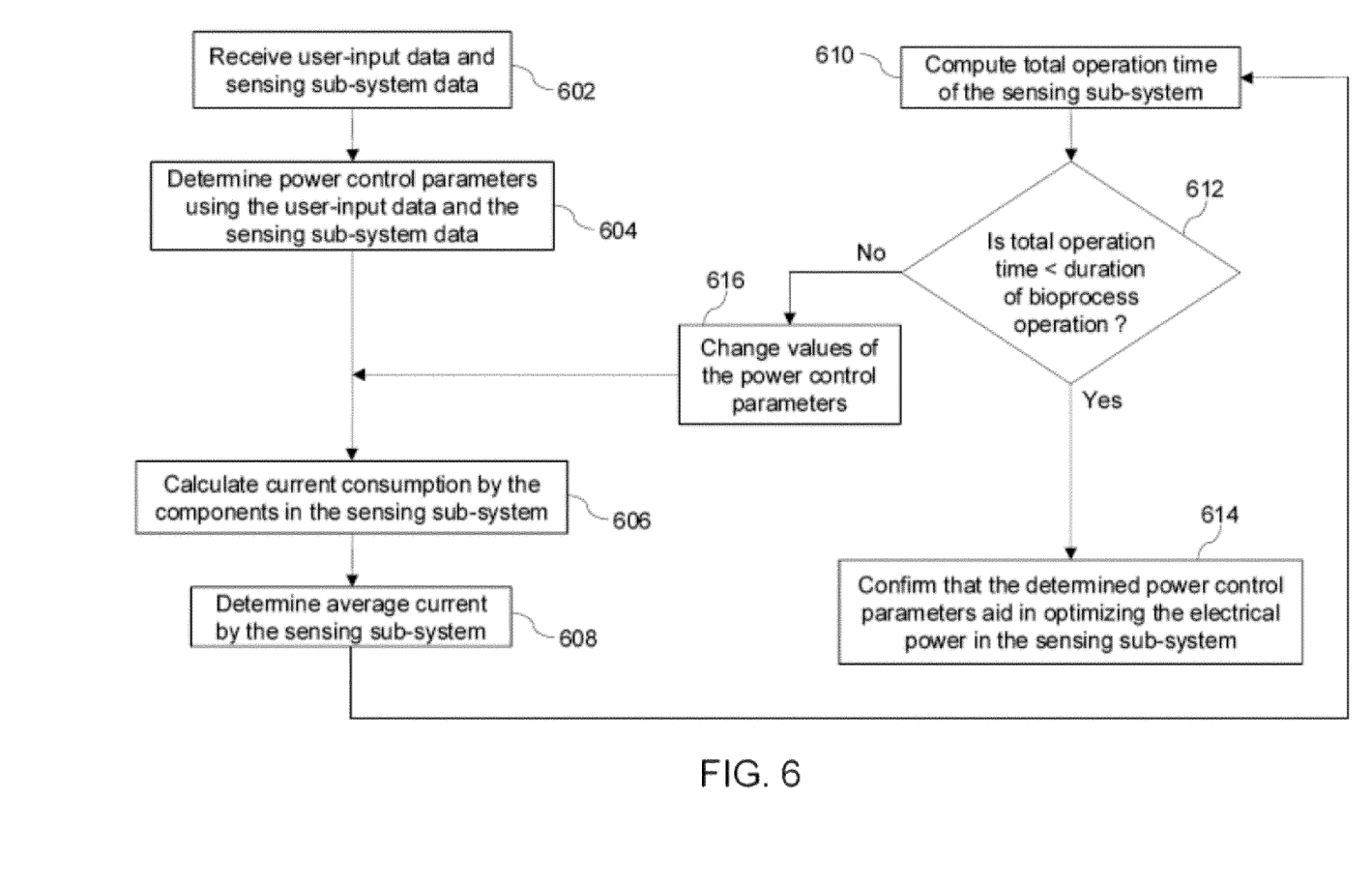
FIG. 6 is a flow chart illustrating a method for determining one or more power control parameters in the control sub-system; in accordance with aspects of the present specification.

In addition, the first controller 112 may verify that the determined power control parameters aid in optimizing the electrical power in the sensing sub-system 102. More specifically, as depicted in step 606, the first controller 112 may determine electrical current consumption of each component in the sensing sub-system 102 using the determined power control parameters. In one example, the first controller 112 may use current ratings of each component included in the sensing sub-system data, the determined power control parameters, such as the connection interval, and the latency to estimate the electrical current consumption of each component in the sensing sub-system 102.

Further, at step 608, the first controller 112 may determine an average current ($I_{avg}$) for the sensing sub-system 102 based on the electrical current consumption of each component and a time duration to complete the cycle of bioprocess operation. The time duration to complete the cycle of bioprocess operation may be included in the user-input data.

Also, at step 610, the first controller 112 may compute a total operation time of the sensing sub-system 102 based on an energy capacity of the power source 110 and the determined average current ($I_{avg}$). The total operation time of the sensing sub-system 102 may be defined as a maximum time duration of operating the sensing sub-system 102.

Furthermore, at step 612, the first controller 112 may verify whether the total operation time of the sensing sub-system 102 is less than the time duration to complete the cycle of bioprocess operation. If the total operation time of the sensing sub-system 102 is less than the time duration to complete the cycle of bioprocess operation, the first controller 112 may confirm that the power control parameters facilitate in optimizing the electrical power in the sensing sub-system 102, as depicted in step 614. If the total operation time of the sensing sub-system 102 is less than the time duration to complete the cycle of bioprocess operation, the first controller 112 may change one or more power control parameters to further reduce the total operation time of the sensing sub-system 102, as depicted in step 616, and the method continues to repeat the steps 606-612. In one example, the first controller 112 may reduce the connection interval from 0.5 sec to 0.3 sec. The first controller 112 may continue to change the values of the one or more power control parameters until the total operation time of the sensing sub-system 102 is less than the time duration to complete the cycle of bioprocess operation.

Further, the first controller 112 transmits the one or more power control parameters to the sensing sub-system 102 to optimize the consumption of the electrical power from the power source 110. In one example, the sensing sub-system 102 may generate one or more switching signals based on the received power control parameters. Further, these switching signals are transmitted to the switch 108 to electrically couple or decouple the sensing unit 106 from the power source 110, which in-turn controls the electrical power transmission from the power source 110 to the sensing unit 106. As a consequence, the electrical power consumption from the power source 110 may be optimized in the sensing sub-system 102. The aspect of optimizing the consumption of the electrical power is described in greater detail with reference to FIGS. 2 and 3.

Referring to FIG. 2, a diagrammatical representation of a bioprocess environment 200 having a sensing sub-system 102 and a control sub-system 104, in accordance with aspects of the present specification, is depicted. The bioprocess environment 200 includes a pump 202, a bioreactor 204, a tubing chamber 206, and one or more tubes 208. It may be noted that the bioprocess environment 200 may include any number of biodevices, and are not limited to the devices shown in FIG. 2. Also, for ease of understanding of the invention, the bioprocess environment 200 is shown with minimal devices.

As depicted in FIG. 2, the pump 202 is coupled to the bioreactor 204 via the tubes 208 and the tubing chamber 206. In one example, these tubes 208 are flexible and disposable plastic tubes. Further, the pump 202 is configured to supply fluid 210 to the bioreactor 204 where the bioprocess operations, such as the cell cultivation takes place. In one example, the bioreactor 204 may include a flexible cell culture bag that aids in cultivating the cells in the fluid 210.

Further, in one embodiment, the sensing sub-system 102 is disposed in the tubing chamber 206 and configured to measure one or more parameters of the fluid 210 conveyed from the pump 202 to the bioreactor 204. In one example, a portion of the sensing sub-system 102 is in contact with the fluid 210 that is flowing through the tubing chamber 206 to measure the parameters of the fluid 210. In the embodiment of FIG. 2, the sensing sub-system 102 includes a sensing unit 106 and a power source 216. The sensing unit 106 includes a sensing element 212 and a signal processor 214. The sensing element 212 is in contact with the fluid 210 in the tubing chamber 206 to sense analog data corresponding to the parameters of the fluid 210. Further, the signal processor 214 is used to process this analog data to generate the parameters of the fluid. More specifically, the signal processor 312 converts the analog data to a digital data that represents the measured parameters of the fluid. Also, as the data is sensed and processed within the sensing unit 218, the sensing sub-system 102 may be referred as a "smart sensor." Moreover, these measured parameters may be stored in the sensing sub-system 102.

Further, the sensing sub-system 102 may be wirelessly coupled to the control sub-system 104 to communicate the measured parameters of the fluid 210 to the control sub-system 104. In one example, the sensing sub-system 102 may transmit one or more signals that represent the measured parameters of the fluid 210. The control sub-system may also be referred to as a "reader" in the art. The control sub-system 104 is disposed external to the sensing sub-systems, in the embodiment illustrated in FIG. 2. Also, the control sub-system 104 is configured to optimize consumption of electrical power in the sensing sub-system 102 using data received from a user and/or data corresponding to the sensing sub-system 102 received from the sensing sub-system 102. The aspect of optimizing the electrical power consumption in the sensing sub-system 102 is described in greater detail earlier and further with reference to FIG. 3.

Figure 3:
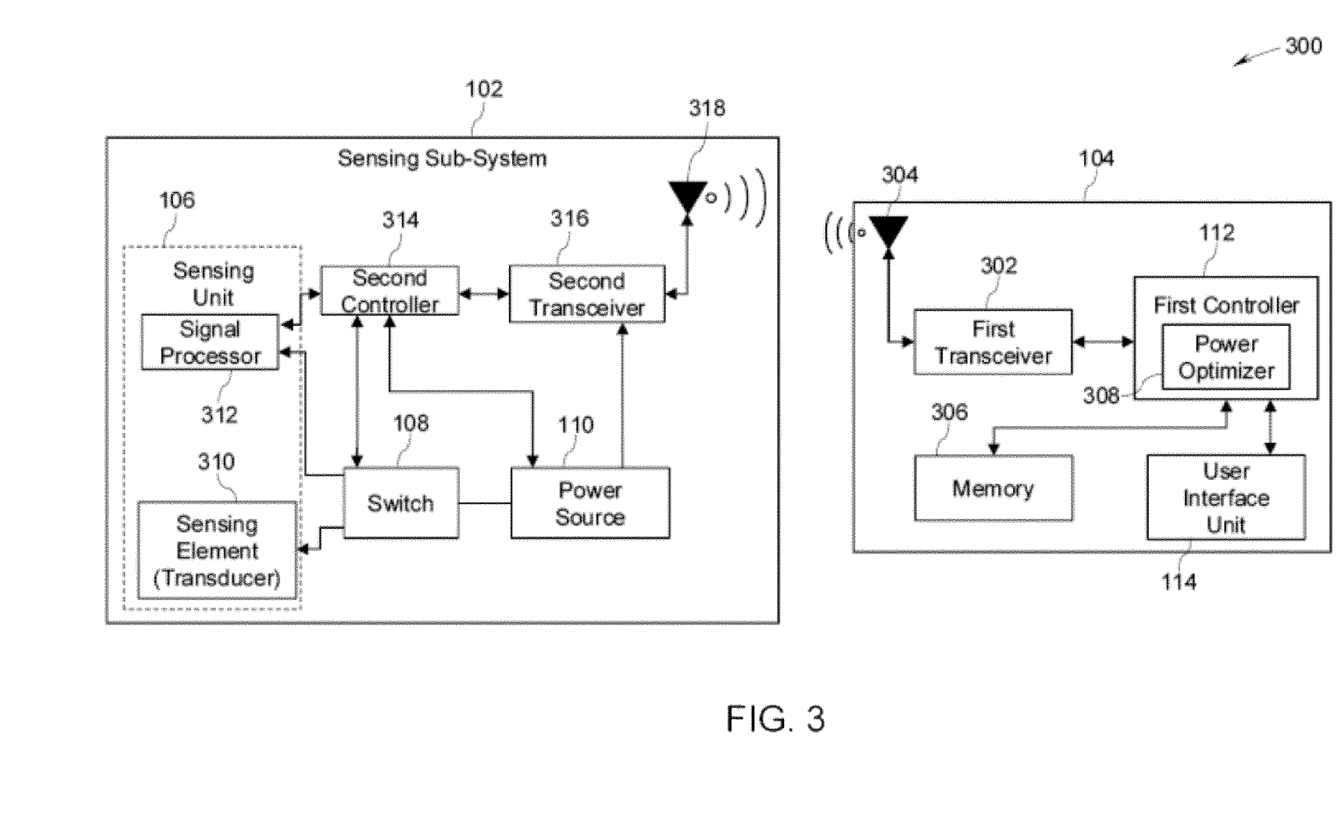
FIG. 3 is a block diagram of a system depicting wireless communication between a sensing sub-system and a control sub-system, in accordance with aspects of the present specification.

Referring to FIG. 3, a block diagram of a system 300 depicting wireless communication between a sensing sub-system 102 and a control sub-system 104, in accordance with one embodiment of the present specification, is depicted. In some embodiments, the control sub-system 104 is a reader that is configured to communicate with one or more sensing sub-systems in the bioprocess environment. Also, the control sub-system 104 is configured to monitor and control the bioprocess operation in the bioprocess environment.

In the illustrated embodiment, in addition to the user interface unit 114 and the first controller 112, the control sub-system 104 includes a first transceiver 302, a first antenna 304, and a memory 306. The first transceiver 304 and the memory 306 are electrically coupled to the first controller 112. The memory 306 may be configured to store the user-input data and the sensing sub-system data received by the user interface unit 112 and/or the first transceiver 302. Also, the memory 306 may be configured to store data corresponding to one or more biodevices and their corresponding bioprocess operations that are employed in the bioprocess environment. In one embodiment, the memory 306 may be configured to store data and program instructions that are accessible by the first controller 112 to perform one or more functions.

Furthermore, the first controller 112 is configured to determine one or more power control parameters based on the user-input data and the sensing sub-system data. In one embodiment, the first controller 112 may include a power optimizer 308 that is configured to execute program instructions in the memory 306 to determine the power control parameters. In one example, the power optimizer 308 may include hardware such as electronic circuits, software, and/or firmware for performing various arithmetic, logical, and graphics processing operations. In another example, the power optimizer 308 may include an integrated circuit (IC) chip that aids in the arithmetic, logical, and graphics processing operations. In certain embodiments, the first controller 112 may display the determined power control parameters to the user via the user interface unit 114.

Further, the first controller 112 transmits the power control parameters to the sensing sub-system 102 via the first transceiver 302 and the first antenna 304. In one example, the power control parameters may be transmitted to the sensing sub-system 102 using any wireless communication techniques, such infrared, short-range radio frequency (RF) communication, Bluetooth, Bluetooth Low Energy (BLE), Wi-Fi, Mesh based protocols e.g. Zigbee, BLE Mesh, ISA100.11a etc, Highway Addressable Remote Transducer (HART) communication, Wi-Max, Global System for Mobile (GSM), General Packet Radio Service (GPRS), Code Division Multiple Access (CDMA), High-Speed Downlink Packet Access (HSDPA), and the like.

As depicted in FIG. 3, the sensing sub-system 102 includes the sensing unit 106, the switch 108, and the power source 110. Further, the sensing unit 106 includes a sensing element 310 and a signal processor 312. The sensing unit 106 may be positioned in such a way that the sensing element 310 is in contact with the fluid employed in the bioprocess operation. Also, the sensing element 310 is configured to sense analog data that is corresponding to the parameters of the fluid. Some of the parameters of the fluid include pressure of the fluid in the bioprocess operation, electrical conductivity of the fluid, a biomass in the fluid, dissolved gas level in the fluid, temperature of the fluid, glucose flow in the fluid, a viable cell density in the fluid, a flow rate of the fluid, a level of foam in the fluid, and a potential of hydrogen (pH) level in the fluid. In one example, the sensing element 310 may include a piezo resistive transducer that is used to sense the pressure of the fluid. In another example, the sensing element 310 may include a thermal transducer that is used to sense the temperature of the fluid. Further, the signal processor 312 receives the sensed analog data from the sensing element 310 and processes this analog data to generate the parameters of the fluid. More specifically, the signal processor 312 converts the analog data to a digital data that represents the measured parameters of the fluid. It may be noted that the sensing element 310 and the signal processor 312 are activated to measure the parameters of the fluid if the switch 108 electrically couples the sensing unit 106 to the power source 110. Also, the sensing element 310 and the signal processor 312 consume electrical power from the power source 110 while measuring the parameters of the fluid. In addition to the sensing unit 106, the switch 108, and the power source 110, the sensing sub-system 102 includes a second controller 314, a second transceiver 316, and a second antenna 318.

As mentioned previously, the sensing sub-system may be single-use in some embodiments. Therefore, in the embodiment illustrated in FIG. 3, all the components of the sensing sub-system 102, such as the sensing unit 106, the switch 108, the power source 110, the second controller 314, and the second transceiver 316 may be disposable. They can suitably be pre-sterilized, e.g. by radiation sterilization or autoclaving, depending on which sterilization methods are compatible with the components. Also, these components may be disposed within the bioprocess device, such as the bioreactor, the tubing chamber, and the pump. In the embodiment of the FIG. 3, these components are disposed within the tubing chamber to measure the parameters of the fluid flowing through the tubing chamber.

Further, the power source 110 may supply electrical power to the second controller 314, the second transceiver 316, and the sensing unit 106. More specifically, the power source 110 provides bias voltage to one or more circuits or integrated chips in the second controller 314, the second transceiver 316, and the sensing unit 106. Further, the second controller 314 is electrically coupled to the switch 108, the second transceiver 316, and the signal processor 312 of the sensing unit 106. Also, the second controller 314 receives the measured parameters of the fluid from the signal processor 312 and transmits the measured parameters to the control sub-system 104 via the second transceiver 316 and the second antenna 318.

In the one embodiment, the second controller 314 is configured to control the electrical power transmission from the power source 110 to the sensing unit 106. Also, the second controller 314 is configured to change a transmission power level of the measured parameters of the fluid to optimize the consumption of the electrical power from the power source 110. More specifically, the power that is used for transmitting the measured parameters of the fluid is reduced to optimize the consumption of the electrical power from the power source 110.

During a cycle of bioprocess operation in the bioprocess environment, the sensing unit 106 measures the parameters of the fluid and transmits the measured parameters to the second controller 314. Further, the second controller 314 transmits the measured parameters to the second transceiver 316 which in-turn transmits the measured parameters at a predetermined power level to the control sub-system 104 via the second antenna 318. In one example, the measured parameters are transmitted as one or more sensed signals to the control sub-system 104.

At the control sub-system 104, the first transceiver 304 receives the parameters of the fluid via the first antenna 304 and transmits these parameters to the first controller 112. The first controller 112 may use these parameters to monitor and control the bioprocess in the bioprocess environment. In one example, if these parameters indicate that the pressure of the fluid is above a predefined pressure value, the first controller 112 may send one or more control signals to the smart switching devices coupled to the tubes to reduce the pressure of the fluid flow in the tubes.

In one embodiment, the first controller 112 is configured for optimizing the electrical power in the sensing sub-system 102. In particular, the first controller 112 determines the power level that is used by the sensing sub-system 102 to transmit the parameters of the fluid. In one embodiment, the first controller 112 may measure a signal strength ratio of the sensed signals representing the parameters of the fluid. Further, the first controller 112 may use the signal strength ratio of the sensed signals to estimate a transmission power value that is required by the sensing sub-system 102 to transmit these parameters of the fluid without any signal loss and/or signal interference. In one example, the signal strength ratio of the sensed signals may be included in the sensing sub-system data received from the sensing sub-system 102 and/or the user interface unit 114.

Further, the first controller 112 determines the power control parameter based on the user-input data and the sensing sub-system data. These power control parameters may include the transmission power value, a switching time value, a connection interval, a handshake power value, number of data bytes, and/or the parameter update rate associated with the sensing sub-system. Upon determining the power control parameters, the first controller 112 transmits these power control parameters from the control sub-system 104 to the sensing sub-system 102.

At the sensing sub-system 102, the second transceiver 316 receives the power control parameters via the second antenna 318 and transmits these power control parameters to the second controller 314. Further, the second controller 314 controls the consumption of electrical power from the power source 110 based on these power control parameters. In one example, if the power control parameters include the switching time value that indicates turn ON time and the turn OFF time of the sensing unit 106, the second controller 314 generates a switching signal that correspond to this switching time value. In one embodiment, the switching signal includes a plurality of pulses having a duty cycle corresponding to the switching time value of the power control parameters. The duty cycle is defined as a fraction of one period in which the switching signal is active. One period is the time taken for a switching signal to complete an on-and-off cycle. The duty cycle of these pulses aid in activating and deactivating the switch 108.

Further, the second controller 314 transmits these switching signals to the switch 108 to decouple the sensing unit 106 from the power source 110 during one or more time intervals indicated by the switching time value. By decoupling the sensing unit 106 from the power source 110 during these time intervals, the electrical power consumption from the power source 110 is reduced, which in-turn may facilitate power source usage for a longer duration to complete the cycle of bioprocess operation in the bioprocess environment.

In another example, if the power control parameters include the transmission power value that indicates the power level of transmitting the measured parameters, the second controller 314 transmits the transmission power value to the second transceiver 316 to adjust or reconfigure power level settings in the second transceiver 316. By adjusting the power level settings in the second transceiver 316, the second transceiver 316 may transmit the measured parameters from the sensing sub-system to the control sub-system with optimal power. More specifically, the second transceiver 316 reduces the electrical power that is required for transmitting these measured parameters to the control sub-system 104. As a result, the electrical power consumption from the power source 110 is reduced.

In a similar manner, the second controller 314 in the sensing sub-system 102 controls the electrical power consumption from the power source 110 based on each of the other power control parameters, such as the connection interval, the handshake power value, the number of data bytes, and the parameter update rate associated with the sensing sub-system 102.

In one embodiment, these power control parameters are reconfigurable based on the change in the user-input data and/or the sensing sub-system data. In such embodiment, the first controller 112 is configured to receive at least one of a power level in the power source 110 and a transmission power value from the sensing sub-system 102, and change the at least one power control parameter based on the at least one of the power level in the power source 110 and the transmission power value. The first controller 112 is further configured to transmit the at least one changed power control parameter to the second controller 314.

For example, after sending the power control parameters to the sensing sub-system 102, the first controller 112 in the control sub-system 104 may receive data indicating a power level of the power source 110 and/or a transmission power value of the second transceiver 316 in the sensing sub-system 102. More specifically, the data may indicate that the power level of the power source 110, such as the battery is below a predefined level. Also, the data may indicate that the second transceiver 316 is transmitting the measured parameters of the fluid at a higher power level. In such circumstances, the first controller 112 may reconfigure or change the power control parameters based on the power level of the power source 110 and/or the transmission power value of the second transceiver 316, to control or reduce the consumption of the electrical power in the sensing sub-system 102. This in-turn facilitates completion of a cycle of the bioprocess operation in the bioprocess environment. In one example, the first controller 112 may change the power transmission value in the power control parameters and may transmit the changed power transmission value in the power control parameters to the second controller 314. Further, the second controller 314 drives the second transceiver 316 to transmit the measured parameters of the fluid at a power level corresponding to the changed power transmission value of the power control parameters. Thus, the consumption of the electrical power from the power source 110 may be further reduced to complete the cycle of bioprocess operation in the bioprocess environment.

Thus, by employing the system, the consumption of the electrical power from the power source is optimized to complete the bioprocess operation in the bioprocess environment. Also, by optimizing the electrical power, the size and the cost of the power source may be reduced.

Figure 4:
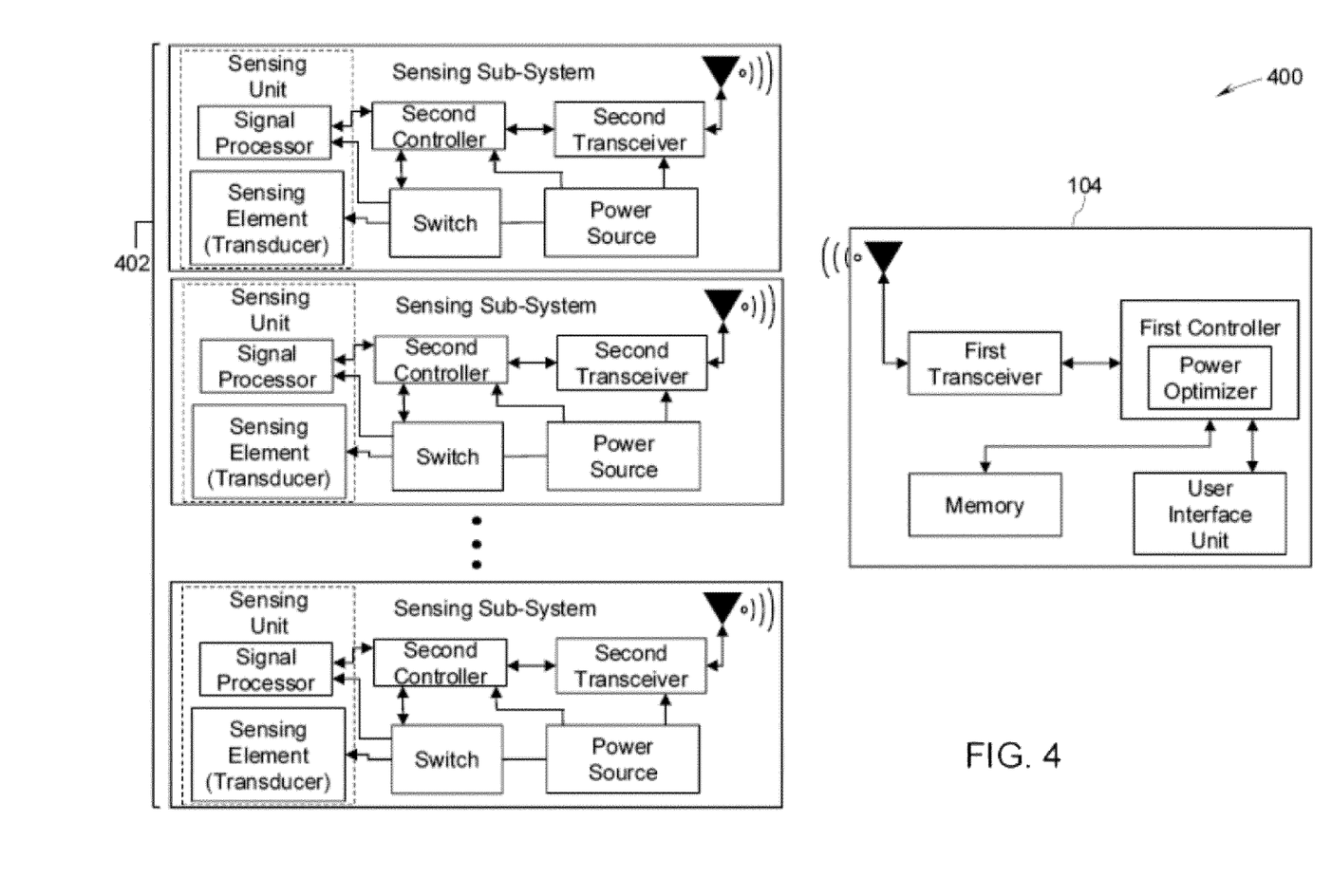
FIG. 4 is another block diagram of a system depicting wireless communication between a plurality of sensing sub-systems and a control sub-system, in accordance with aspects of the present specification.

Referring to FIG. 4, a block diagram of a system 400 depicting wireless communication between a plurality of wireless sensing sub-systems 402 and a control sub-system 404, in accordance with one embodiment of the present specification, is depicted. It may be noted that each of the wireless sensing subsystems 402 is similar to the sensing sub-system 102 shown in FIG. 3. It may be further noted that the system 400 may include any number of sensing sub-systems 402, and is not limited to the number of sensing sub-systems 402 depicted in FIG. 4

In the embodiment of FIG. 4, the plurality of wireless sensing sub-systems 402 are single-use and are configured to be employed in a bioprocess environment. Further, each of the wireless sensing sub-systems 402 includes a sensing unit configured to measure at least one parameter of the bioprocess environment and a power source electrically coupled to the sensing unit and configured to transmit an electrical power to the sensing unit. Also, each of the wireless sensing sub-systems 402 includes a switch configured to electrically couple or decouple the sensing unit from the power source.

Further, the control sub-system 104 is wirelessly coupled to the plurality of wireless sensing sub-systems 402. Also, the control sub-system 104 includes a first controller configured to determine at least one power control parameter based on a user-input data and a sensing sub-system data of a corresponding wireless sensing sub-system. Further, the controller is configured to optimize consumption of the electrical power in the corresponding wireless sensing sub-system, based on the power control parameter.

In particular, the control sub-system 104 determines one or more power control parameters for the corresponding wireless sensing subsystem 402 based on the user-input data and the sensing sub-system data of the corresponding wireless sensing sub-system. It may be noted that the user-input data and the sensing sub-system data may be same or different for each of the wireless sensing sub-systems 402 depending to a type of the wireless sensing sub-system, an application of the wireless sensing sub-system, and/or parameters to be measured by the wireless sensing sub-system. If the user-input data and the sensing sub-system data are different for the sensing sub-systems 402, the power control parameters determined by the control sub-system 104 may also be different for the wireless sensing sub-systems 402. Further, these power control parameters are transmitted to their respective wireless sensing sub-system to optimize consumption of the electrical power in the corresponding wireless sensing sub-system.

Figure 5:
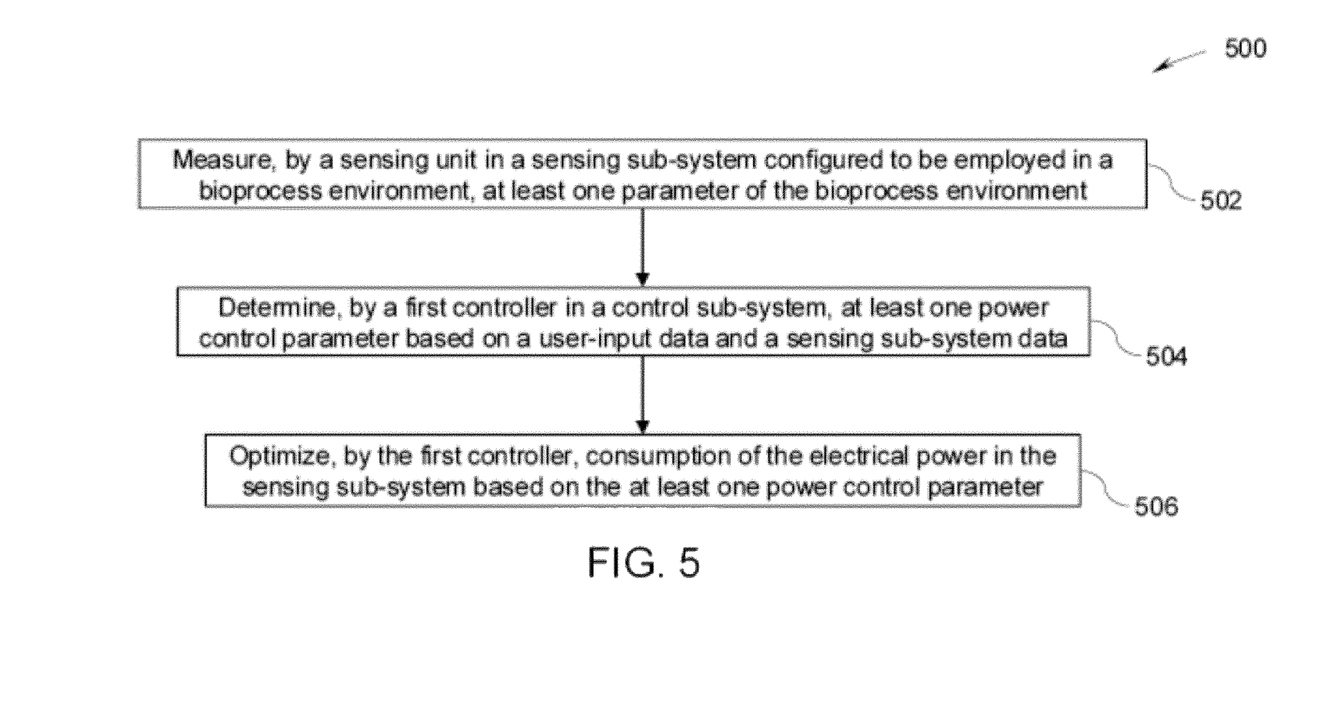
FIG. 5 is a flow chart illustrating a method for enabling a wireless sensor by optimizing electrical power, in accordance with aspects of the present specification.

Referring to FIG. 5, a flow chart illustrating a method 500 for optimizing consumption of an electrical power in a bioprocess environment, in accordance with aspects of the present specification, is depicted. For ease of understanding, the method 500 is described with reference to the components of FIGS. 1-4. The method 500 begins with measuring, by a sensing unit in a sensing sub-system configured to be employed in a bioprocess environment, at least one parameter of the bioprocess environment, as shown in step 502. In particular, the sensing unit includes a sensing element that is in contact with the fluid and configured to sense the analog data that is corresponding to the parameters of the fluid. Further, the sensing unit includes a signal processor that is coupled to the sensing element and configured to process the analog data to determine the parameters of the fluid in a digital form. Further, these parameters are transmitted from the sensing sub-system to the control sub-system.

Subsequently, at step 504, the method includes determining, by a first controller in a control sub-system, at least one power control parameter based on a user-input data and a sensing sub-system data. In one embodiment, the user may select one or more options from a drop-down menu in the user interface unit. These options may include an application of the sensing sub-system, duration of a bioprocess operation of the bioprocess device, such as the bioreactor, and the desired parameters to be measured from the fluid supplied to the bioreactor. Further, the user interface unit transmits the selected options as the user-input data to the first controller in the control sub-system. Also, the first controller may receive the sensing sub-system data from the sensing sub-system and/or the user interface unit. The sensing sub-system data includes data indicating a type of the sensing sub-system, an electrical power consumption of the sensing sub-system, and/or a power level in the power source of the sensing sub-system. Further, the first controller may include the power optimizer that is configured to execute program instructions in the memory to determine the power control parameters based on the sensing sub-system data and the user-input data. The power control parameters may include a transmission power value, a switching time value, a connection interval, a handshake power value, number of data bytes, and the parameter update rate associated with the sensing sub-system.

In addition, at step 506, the method includes optimizing, by the first controller, consumption of the electrical power in the sensing sub-system based on the at least one power control parameter. In particular, the controller transmits the one or more power control parameters to the sensing sub-system. In one example, the second controller in the sensing sub-system may generate one or more switching signals based on the received power control parameters. Further, these switching signals are transmitted to the switch to electrically couple or decouple the sensing unit from the power source, which in-turn controls the electrical power transmission from the power source to the sensing unit. As a consequence, the electrical power consumption from the power source is optimized in the sensing sub-system.

The various embodiments of the system and method aid in optimizing consumption of an electrical power in a sensing sub-system disposed in a bioprocess environment. By optimizing the consumption of the electrical power, the size of the power source, such as a battery in the wireless sensing sub-systems may be reduced. This in-turn may reduce the size and the manufacturing cost of the wireless sensing sub-systems.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
   a sensing sub-system configured to be employed in a bioprocess environment, the sensing sub-system comprising:
   one or more sensing units configured to measure at least one parameter of the bioprocess environment or to detect a correct connection of two connector units,
   a portable battery power source electrically coupled to the one or more sensing units and configured to transmit an electrical power to the one or more sensing units, and
   a switch configured to electrically couple or decouple the one or more sensing units from the power source; and
   a control sub-system comprising a first controller configured to:
   determine at least one power control parameter based on a user-input data and a sensing sub-system data, and
   optimize consumption of the electrical power in the sensing sub-system, based on the power control parameter, wherein optimizing consumption of the electrical power in the sensing sub-system comprises:
   a) calculating current consumption by the components in the sensing sub-system,
   b) determining average current for the sensing sub-system;
   c) computing total operation time of the sensing sub-system;
   d) determining if a total operation time of the sensing sub-system is less than a time duration to complete a cycle of bioprocess operation; and,
   i) changing the power control parameter if the total operation time of the sensing sub-system is less than the time duration to complete the cycle of bioprocess operation, or
   ii) confirming that the power control parameter aid in optimizing the electrical power in the sensing sub-system if the total operation time of the sensing sub-system is greater than the time duration to complete the cycle of bioprocess operation,
   wherein the sensing sub-system is wirelessly coupled to the control sub-system to wirelessly communicate the measured at least one parameter to the control sub-system.

2. The system of claim 1, wherein the control sub-system is disposed external to the sensing sub-system, and the control sub-system further comprises a first transceiver electrically coupled to the first controller and configured to transmit the at least one power control parameter to the sensing sub-system; and wherein the sensing sub-system further comprises:
   a second transceiver wirelessly coupled to the first transceiver and configured to receive the at least one power control parameter, and
   a second controller electrically coupled to the second transceiver and configured to control the consumption of the electrical power based on the at least one power control parameter.

3. The system of claim 2, wherein the second controller is electrically coupled to the switch and configured to:

generate a switching signal based on the at least one power control parameter; and transmit the switching signal to the switch to control the electrical power transmission from the power source to the one or more sensing units.

4. The system of claim 3, wherein the switching signal comprises a plurality of pulses having a duty cycle corresponding to the at least one power control parameter.

5. The system of claim 2, wherein the second controller is electrically coupled to the second transceiver and configured to control a power level of a plurality of sensed signals transmitted from the one or more sensing units via the second transceiver, wherein the sensed signals represent the at least one measured parameter of the bioprocess environment.

6. The system of claim 1, wherein the at least one power control parameter comprises a transmission power value, a switching time value, a connection interval, a handshake power value, number of data bytes, and a parameter update rate associated with the sensing sub-system.

7. The system of claim 1, wherein the user-input data comprises data indicating at least one of time duration of operating the sensing sub-system, application of the sensing sub-system, and at least one desired parameter of a fluid in the bioprocess environment.

8. The system of claim 1, wherein the sensing sub-system data comprises data indicating at least one of type of the sensing sub-system and power consumption of the sensing sub-system.

9. The system of claim 1, wherein the sensing sub-system is a single-use device that is disposable after a cycle of bioprocess operation.

10. The system of claim 1, wherein the at least one measured parameter of the bioprocess environment comprises pressure of a fluid in the bioprocess environment, electrical conductivity of the fluid, dissolved gas level in the fluid, temperature of the fluid, glucose flow in the fluid, a potential of hydrogen (pH) level in the fluid, a cell viability in the fluid, a flow rate of the fluid, and a level of foam in the fluid.

11. The system of claim 2, wherein the first controller is configured to:

receive at least one of a power level in the power source and a transmission power value from the sensing sub-system, change the at least one power control parameter based on the at least one of the power level in the power source and the transmission power value, and transmit the at least one changed power control parameter to the second controller.

12. The system of claim 2, wherein the second controller is configured to control the consumption of the electrical power based on the at least one changed power control parameter.

13. The system of claim 1, wherein the sensing sub-system is coupled to a bioreactor comprising a flexible cell culture bag.

14. A method comprising:

powering, by a portable battery, a wireless sensing unit in a sensing sub-system configured to be employed in a bioprocess environment, measuring, by sensing, at least one parameter of the bioprocess environment, or detecting by a pair of sensing units if two connector units have been correctly connected;

determining, by a first controller in a control sub-system, at least one power control parameter based on a user-input data and a sensing sub-system data wirelessly received from the wireless sensing unit; and optimizing, by the first controller, consumption of the electrical power in the sensing sub-system based on the at least one power control parameter;

wherein optimizing consumption of the electrical power in the sensing sub-system comprises:

a) calculating current consumption by the components in the sensing sub-system, b) determining average current for the sensing sub-system;

c) computing total operation time of the sensing sub-system;

d) determining if a total operation time of the sensing sub-system is less than a time duration to complete a cycle of bioprocess operation; and, i) changing the power control parameter if the total operation time of the sensing sub-system is less than the time duration to complete the cycle of bioprocess operation, or ii) confirming that the power control parameter aid in optimizing the electrical power in the sensing sub-system if the total operation time of the sensing sub-system is greater than the time duration to complete the cycle of bioprocess operation.

15. The method of claim 14, further comprising:

wirelessly transmitting, by a first transceiver in the control sub-system, the at least one power control parameter to the sensing sub-system;

receiving, by a second transceiver in the sensing sub-system, the at least one power control parameter from the first transceiver; and controlling, by a second controller in the sensing sub-system, the consumption of the electrical power based on the at least one power control parameter.

16. The method of claim 15, wherein controlling, by the second controller in the sensing sub-system, the consumption of the electrical power comprises:

generating, by the second controller, a switching signal based on the at least one power control parameter; and transmitting, by the second controller, the switching signal to the switch to control the electrical power transmission from the power source to the one or more sensing units.

17. The method of claim 16, wherein the switching signal comprises a plurality of pulses having a duty cycle corresponding to the at least one power control parameter.

18. The method of claim 15, wherein controlling, by the second controller in the sensing sub-system, the consumption of the electrical power comprises controlling, by the second controller, a power level of a plurality of sensed signals transmitted from the one or more sensing units via the second transceiver, wherein the sensed signals represent the at least one parameter of the bioprocess environment.

19. The method of claim 14, wherein the power control parameter comprises a transmission power value, a switching time value, a connection interval, a handshake power value, number of data bytes, and a parameter update rate associated with the sensing sub-system.

20. The method of claim 14, wherein the user-input data comprises data indicating at least one of time duration of operating the sensing sub-system, application of the sensing sub-system, and at least one desired parameter of fluid in the bioprocess environment.

21. The method of claim 14, wherein the sensing sub-system is a single-use device that is disposable after a cycle of bioprocess operation.

22. The method of claim 14, wherein the at least one measured parameter of the bioprocess environment comprises pressure of a fluid in the bioprocess environment, electrical conductivity of the fluid, dissolved gas level in the fluid, temperature of the fluid, glucose flow in the fluid, a potential of hydrogen (pH) level in the fluid, a cell viability in the fluid, a flow rate of the fluid, and a level of foam in the fluid.

23. The method of claim 14, wherein the bioprocess environment comprises a bioreactor comprising a flexible cell culture bag.

24. A system comprising:
   a plurality of wireless sensing sub-systems that are single-use and configured to be employed in a bioprocess environment, wherein each of the plurality of wireless sensing sub-systems comprises:
      a sensing unit configured to measure at least one parameter of the bioprocess environment,
      a portable battery power source electrically coupled to the sensing unit and configured to transmit an electrical power to the sensing unit, and
      a switch configured to electrically couple or decouple the sensing unit from the power source; and
   a control sub-system wirelessly coupled to the plurality of wireless sensing sub-systems to wirelessly receive a sensing sub-system data, wherein the control sub-system comprises a first controller configured to:
   determine at least one power control parameter based on a user-input data and the sensing sub-system data of a corresponding wireless sensing sub-system, and
   optimize consumption of the electrical power in the corresponding wireless sensing sub-system, based on the at least one power control parameter by:
      a) calculating current consumption by the components in the sensing sub-system,
      b) determining average current for the sensing sub-system;
      c) computing total operation time of the sensing sub-system;
      d) determining if a total operation time of the sensing sub-system is less than a time duration to complete a cycle of bioprocess operation; and,
         i) changing the power control parameter if the total operation time of the sensing sub-system is less than the time duration to complete the cycle of bioprocess operation, or
         ii) confirming that the power control parameter aid in optimizing the electrical power in the sensing sub-system if the total operation time of the sensing sub-system is greater than the time duration to complete the cycle of bioprocess operation.

\* \* \* \* \*